United States Patent
Gooding, Jr. et al.

[11] Patent Number: 5,595,807
[45] Date of Patent: Jan. 21, 1997

[54] COMBINATION WET DRY WIPE

[76] Inventors: Robert B. Gooding, Jr.; Kimberly Minor, both of 124 Federal St., St. Albans, Vt. 05478

[21] Appl. No.: 457,126

[22] Filed: Jun. 1, 1995

[51] Int. Cl.⁶ .......................... A61F 13/00; A61F 13/15; A61K 9/70; A61M 35/00

[52] U.S. Cl. .............. 428/80; 424/402; 428/74; 428/76; 428/213; 428/286

[58] Field of Search .................. 424/402; 428/286, 428/80, 213

[56] References Cited

U.S. PATENT DOCUMENTS

| | | | |
|---|---|---|---|
| 4,198,407 | 12/1979 | Rubens | 428/286 |
| 4,522,203 | 6/1985 | Mays | 428/286 |
| 4,741,944 | 5/1988 | Jackson et al. | 428/286 |
| 4,837,078 | 6/1989 | Harrington | 428/286 |
| 4,948,585 | 8/1990 | Schlein | 428/286 |
| 5,079,792 | 1/1992 | D'Han | 428/286 |
| 5,087,450 | 2/1992 | Lister | 428/286 |
| 5,238,750 | 8/1993 | Niehaus et al. | 428/286 |
| 5,530,817 | 7/1994 | Arnott et al. | 428/286 |

*Primary Examiner*—James C. Cannon

[57] ABSTRACT

A wipe for wetting and subsequently drying portions of the human body. The inventive device includes a wetting pad for applying a topical cleansing solution to a body part. An absorbing pad is coupled to the wetting pad for drying the cleansed body part subsequent to cleaning thereof.

6 Claims, 3 Drawing Sheets

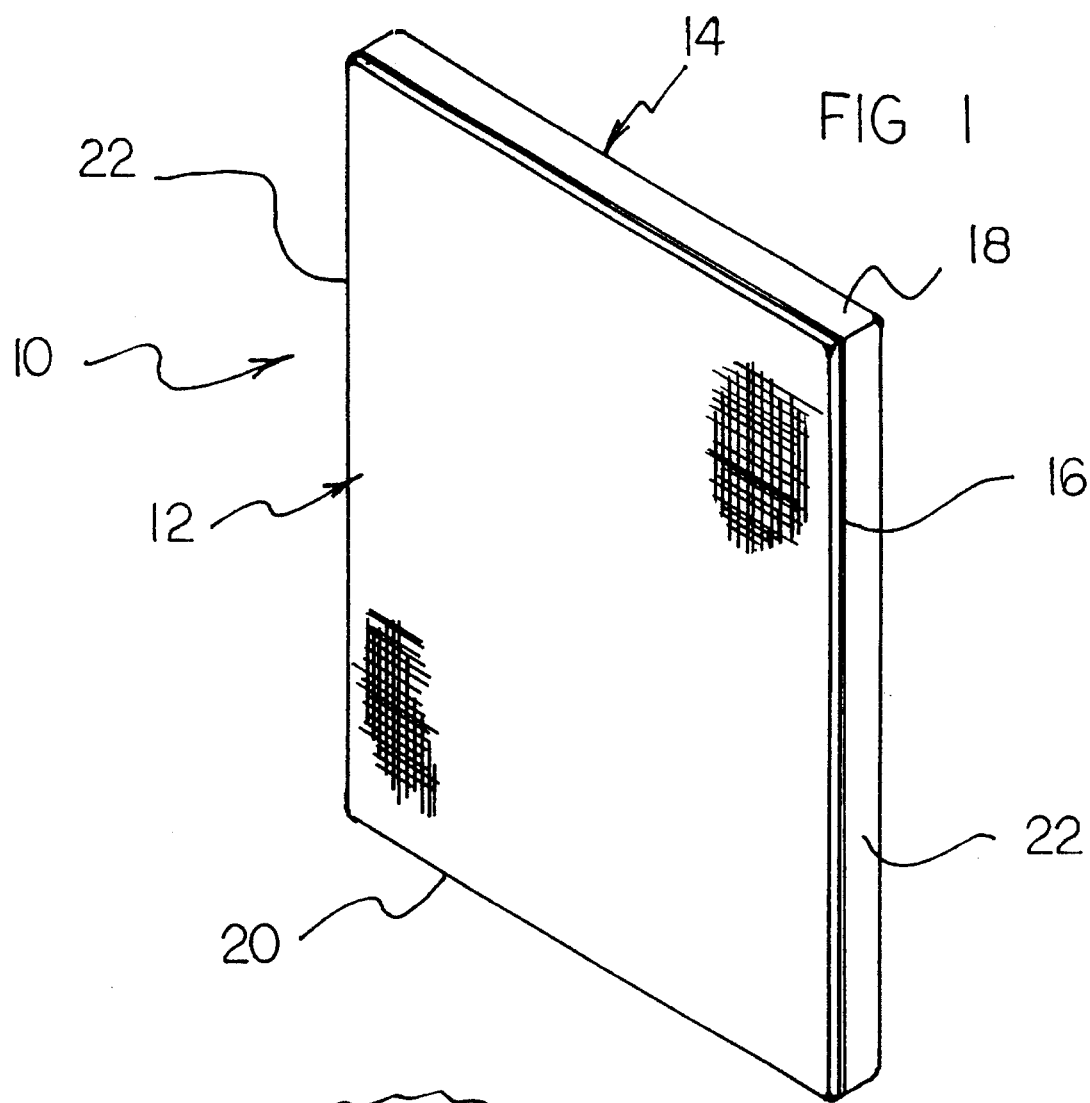
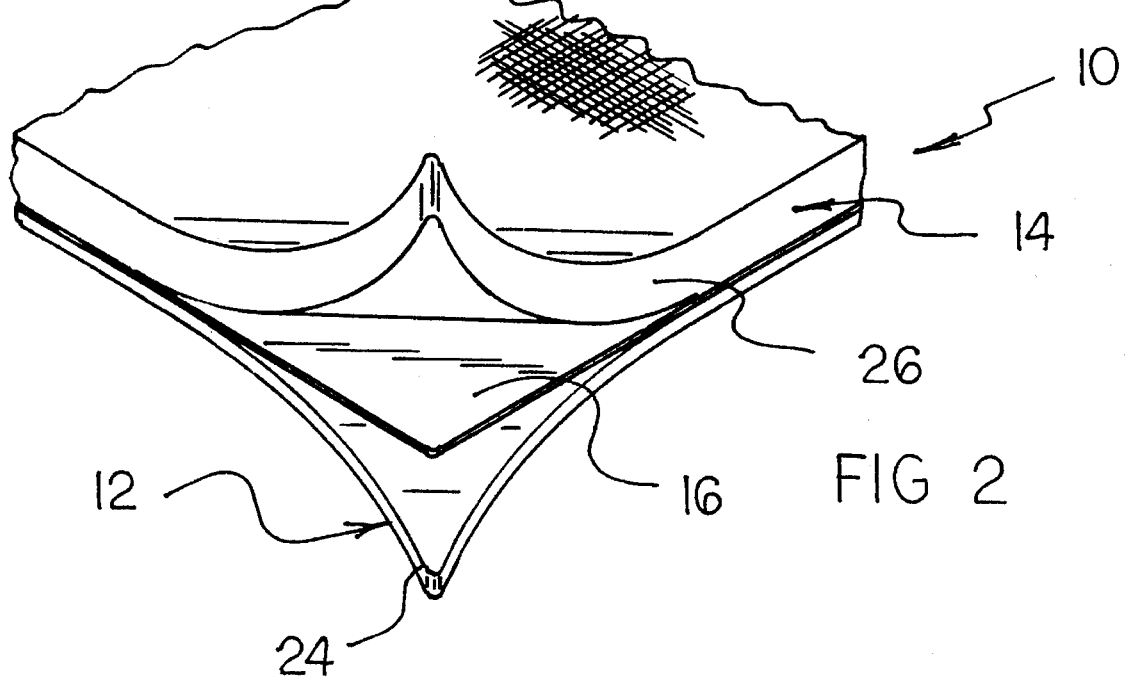

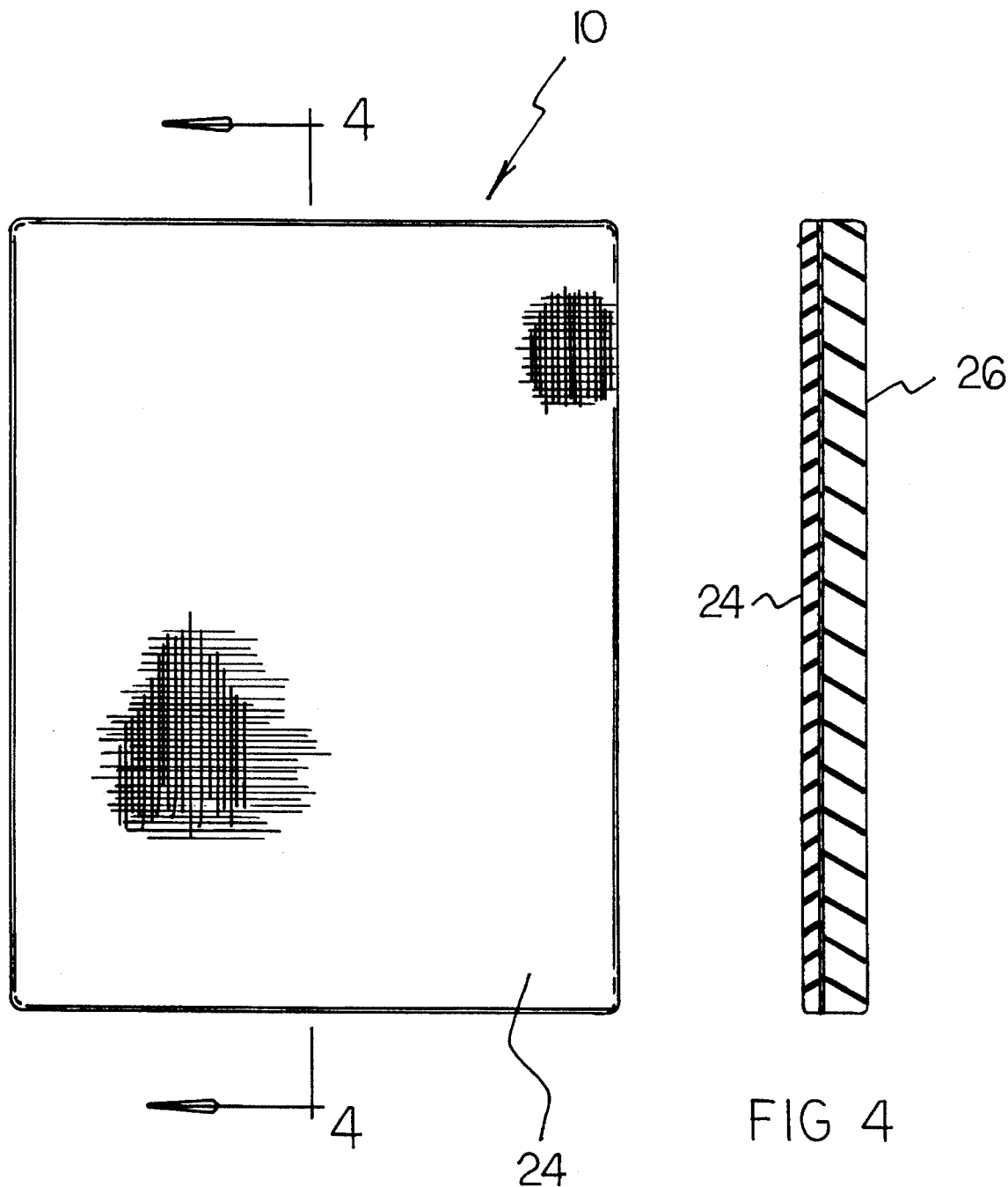

COMBINATION WET DRY WIPE

BACKGROUND OF THE INVENTION

1. Field of the Invention

The present invention relates to cleaning devices and more particularly pertains to a combination wet dry wipe for wetting and subsequently drying portions of the human body.

2. Description of the Prior Art

The use of cleaning devices is known in the prior art. More specifically, cleaning devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art cleaning devices include U.S. Pat. No. 4,753,844; U.S. Pat. No. 3,520,016; U.S. Pat. No. 4,853,281; U.S. Pat. No. 4,837,078; U.S. Pat. No. 4,741,944; and U.S. Pat. No. 4,586,606.

While these devices fulfill their respective, particular objectives and requirements, the aforementioned patents do not disclose a combination wet dry wipe for wetting and subsequently drying portions of the human body which includes a wetting means for applying a topical cleansing solution to a body part, and an absorbing means coupled to the wetting means for drying the cleansed body part subsequent to cleaning thereof.

In these respects, the combination wet dry wipe according to the present invention substantially departs from the conventional concepts and designs of the prior art, and in so doing provides an apparatus primarily developed for the purpose of wetting and subsequently drying portions of the human body.

SUMMARY OF THE INVENTION

In view of the foregoing disadvantages inherent in the known types of cleaning devices now present in the prior art, the present invention provides a new combination wet dry wipe construction wherein the same can be utilized for effecting cleaning and drying of parts of the human body. As such, the general purpose of the present invention, which will be described subsequently in greater detail, is to provide a new combination wet dry wipe apparatus and method which has many of the advantages of the cleaning devices mentioned heretofore and many novel features that result in a combination wet dry wipe which is not anticipated, rendered obvious, suggested, or even implied by any of the prior art cleaning devices, either alone or in any combination thereof.

To attain this, the present invention generally comprises a wipe for wetting and subsequently drying portions of the human body. The inventive device includes a wetting pad for applying a topical cleansing solution to a body part. An absorbing pad is coupled to the wetting pad for drying the cleansed body part subsequent to cleaning thereof.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new combination wet dry wipe apparatus and method which has many of the advantages of the cleaning devices mentioned heretofore and many novel features that result in a combination wet dry wipe which is not anticipated, rendered obvious, suggested, or even implied by any of the prior art tool guides, either alone or in any combination thereof.

It is another object of the present invention to provide a new combination wet dry wipe which may be easily and efficiently manufactured and marketed.

It is a further object of the present invention to provide a new combination wet dry wipe which is of a durable and reliable construction.

An even further object of the present invention is to provide a new combination wet dry wipe which is susceptible of a low cost of manufacture with regard to both materials and labor, and which accordingly is then susceptible of low prices of sale to the consuming public, thereby making such combination wet dry wipes economically available to the buying public.

Still yet another object of the present invention is to provide a new combination wet dry wipe which provides in the apparatuses and methods of the prior art some of the advantages thereof, while simultaneously overcoming some of the disadvantages normally associated therewith.

Still another object of the present invention is to provide a new combination wet dry wipe for wetting and subsequently drying portions of the human body.

Yet another object of the present invention is to provide a new combination wet dry wipe which includes a wetting means for applying a topical cleansing solution to a body part, and an absorbing means coupled to the wetting means for drying the cleansed body part subsequent to cleaning thereof.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an isometric illustration of a combination wet dry wipe according to the present invention.

FIG. 2 is a partially exploded isometric illustration of a portion of the present invention.

FIG. 3 is an elevation view of the invention.

FIG. 4 is a cross sectional view taken along line 4—4 of FIG. 3.

DESCRIPTION OF THE PREFERRED EMBODIMENT

Figure 5:
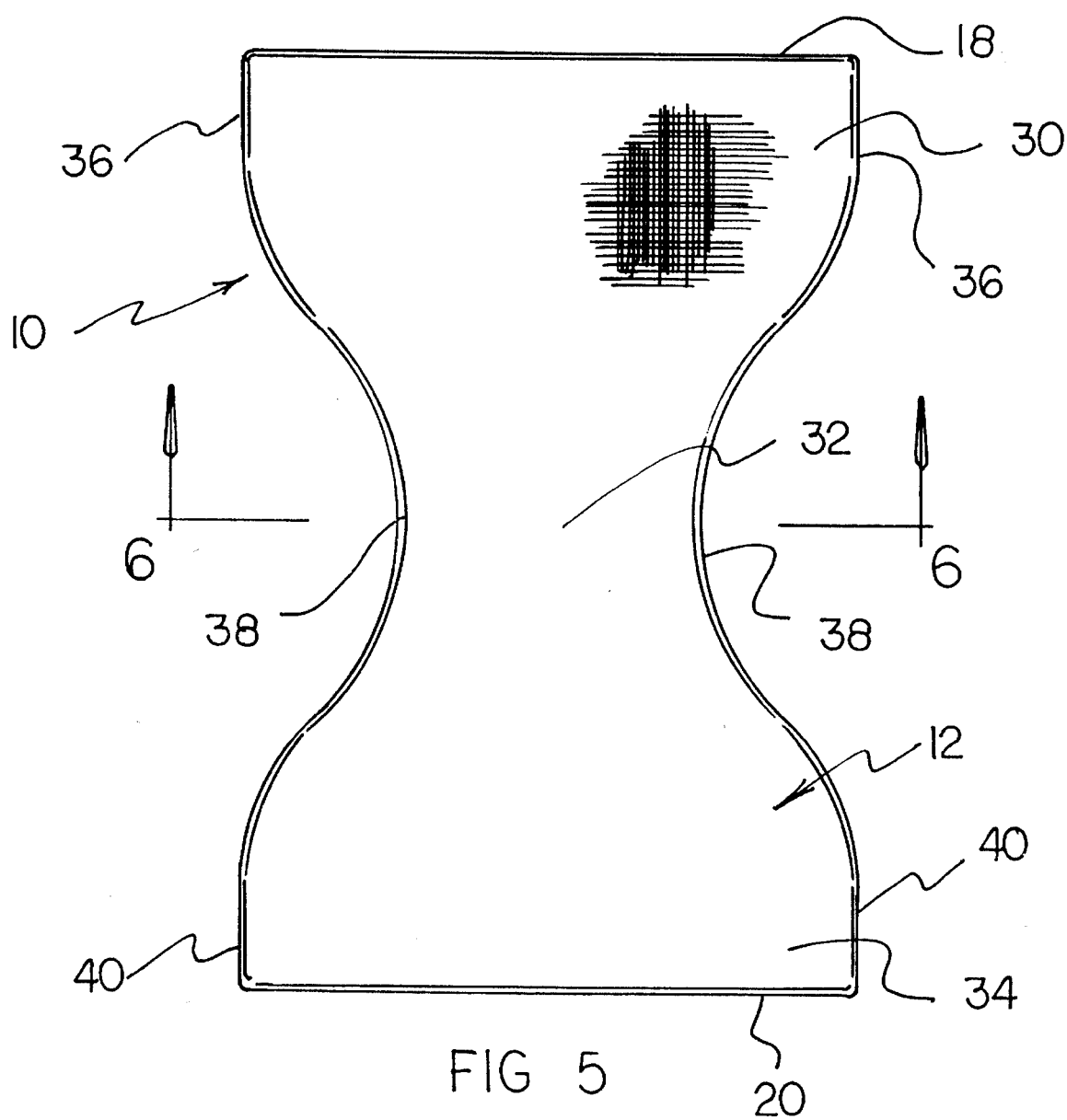
FIG. 5 is an elevation view of an alternative form of the present invention.

With reference now to the drawings, and in particular to FIGS. 1–6 thereof, a combination wet dry wipe embodying the principles and concepts of the present invention and generally designated by the reference numeral 10 will be described.

More specifically, it will be noted that the combination wet dry wipe 10 comprises a wetting means 12 for retaining a topical cleansing solution and permitting manual application of such topical cleansing solution to an object such as a portion of a human body. An absorbing means 14 is coextensively coupled to the wetting means 12 and operates for drying an object such as a portion of the human body subsequent to cleansing thereof by the wetting means 12. An impermeable separating layer 16 is interposed between the absorbing means 14 and the wetting means 12 so as to preclude absorption by the absorbing means 14 of the topical cleansing solution impregnated in the wetting means 12. By this structure, an individual can effect both cleaning and drying of various body parts as desired.

As best illustrated in FIGS. 1 through 4, it can be shown that the wetting means 12 and the coextensively aligned absorbing means 14 cooperate with the impermeable separating layer 16 so as to define a linear top edge 18 spaced from and oriented substantially parallel to a linear lower edge 20. Further, linear lateral edges 22 project substantially orthogonally between the top and bottom edges 18 and 20 so as to define a substantially rectangular shape of the combination wet dry wipe 10 as shown in the drawings.

With continuing reference to FIGS. 2 through 4, it can be shown that the wetting means 12 of the present invention 10 preferably comprises a saturated layer 24 of fabric material which is preferably disposable. Examples of suitable materials include paper towels or paper napkins, or any other fiber fabric or foam material capable of retaining a topical cleansing solution. The saturated layer 24 is secured to the impermeable separating layer 16 by a suitable adhesive interposed therebetween. Alternatively, the saturated layer 24 can be secured to the separating layer 16 by stitching or other mechanical fastening means. The absorbing means 14 comprises an absorbent layer 26 similarly formed of a flexible fabric material such as a paper towel or paper napkin or any other fiber based or porous foam material. The absorbent layer 26 coextensively covers the separating layer 16 and is adhesively or otherwise mechanically fastened thereto so as to project in a direction opposite that of the saturated layer 24. Preferably and as best illustrated in FIG. 4, it can be shown that the saturated layer 24 is of a first thickness, with the absorbent layer 26 being of a second thickness, wherein the second thickness is substantially greater than the first thickness. The separating layer 16 can be formed of any conventionally known polymeric material such as plastic or the like and may alternatively be heat-sealed to the adjacent layers 24 and 26 of the respective wetting means 12 and absorbing means 14. In other words, the separating layer 16 can be formed of a thermoplastic material, wherein heating of the invention 10 during construction thereof will result in an adhesive bond being created between the thermoplastic material and the layers 24 and 26.

The topical cleansing solution impregnated into the saturated layer 24 of the wetting means 12 preferably comprises an antiseptic or sterilizing solution. Such solution may or may not comprise an alcohol mixture.

Figure 6:
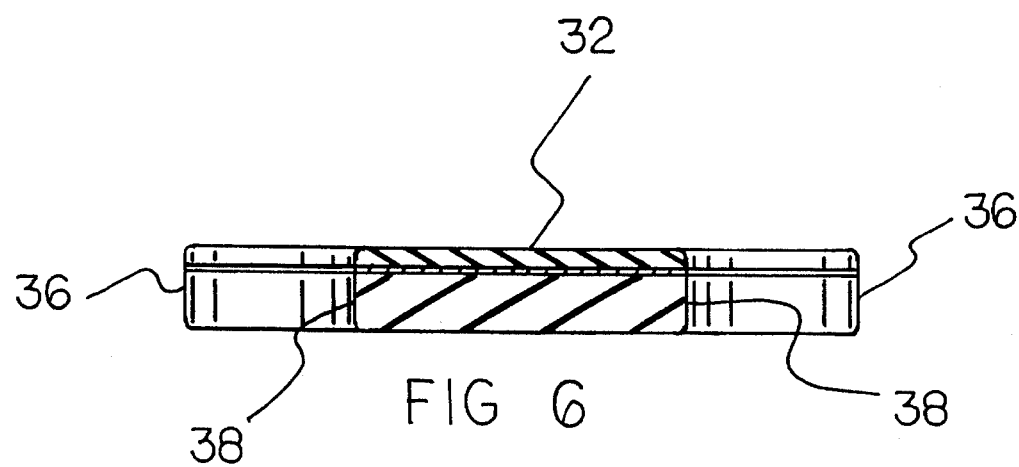
FIG. 6 is cross sectional view taken along in 6—6 of FIG. 5.

Referring now to FIGS. 5 and 6 wherein an alternative form of the present invention 10 is illustrated in detail, it can be shown that the separating layer 16, the saturated layer 24, and the absorbent layer 26 of the device 10 can be coextensively configured so as to define an upper porion 30 continuing into a medial portion 32 and terminating in a lower portion 34. The upper portion 30 is characterized by linear upper lateral edges 36 projecting substantially orthogonally from opposed ends of the linear top edge 18 thereof. The linear upper lateral edges 36 integrally continue into arcuate center edges 38 of the medial portion 32. The arcuate center edges 38 are each shaped so as to define a radius of curvature having a center point located laterally of the device 10. In other words, the arcuate center edges 38 operate to reduce a transverse width of the device 10 along the medial portion 32 thereof. The arcuate center edges 38 continue into linear lower lateral edges 40 which project substantially orthogonally from opposed ends of the linear lower edge 20. By this structure, the device 10 assumes an hourglass-shape which permits the upper portion 30 to be twisted relative to the lower portion 34 as the medial portion 32 is wrapped about or otherwise engaged to various portions of the human body.

In use, the combination wet dry wipe 10 according to the present invention can be easily utilized to effect cleansing of various portions of the human body. The device 10 is particularly suited for the cleansing of genital portions of the human body subsequent to the performance of a sexual act.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A combination wet dry wipe comprising:

a wetting means for retaining a topical cleansing solution and permitting manual application of the topical cleansing solution to an object, the wetting means being comprised of a saturated layer of fabric material saturated with a topical cleansing solution, the saturated layer is of a first thickness;

an absorbing means coupled to the wetting means for drying an object, the absorbing means being comprised of an absorbent layer of flexible fabric material, the absorbent layer being of a second thickness, wherein the second thickness is substantially greater than the first thickness of the saturated layer;

an impermeable separating layer interposed between the absorbing means and the wetting means, the separating layer being formed of thermoplastic material and having the saturated layer secured thereto by an adhesive interposed therebetween, the separating layer having the absorbent layer coextensively covering and being adhesively fastened thereto so as to project in a direction opposite that of the saturated layer; and whereby the wetting means, the separating layer and the absorbing means are coextensive, the wetting means and the coextensive absorbing means cooperate with the coextensive impermeable separating layer so as to define a linear top edge, a linear lower edge spaced from and oriented substantially parallel to the linear top edge, and linear lateral edges extending substantially orthogonally between the top and bottom edges so as to define a substantially rectangular shape of the combination wet dry wipe.

2. The combination wet dry wipe of claim 1, wherein the separating layer, the saturated layer, and the absorbent layer are coextensively configured so as to define an upper porion continuing into a medial portion and terminating in a lower portion.

3. The combination wet dry wipe of claim 2, wherein the upper portion is of a first transverse width, and the medial portion is of a second transverse width, wherein the first transverse width is substantially greater than the second transverse width.

4. The combination wet dry wipe of claim 3, wherein the lower portion is of the first transverse width.

5. The combination wet dry wipe of claim 4, wherein the upper portion includes a linear top edge with linear upper lateral edges projecting substantially orthogonally from opposed ends of the linear top edge, the linear upper lateral edges continuing into arcuate center edges of the medial portion, the arcuate center edges each being shaped so as to define a radius of curvature having a center point located laterally of the medial portion, wherein the lower portion includes linear lower lateral edges continuing from the arcuate center edges, and a linear lower edge, with the linear lower lateral edges extending substantially orthogonally from opposed ends of the linear lower edge.

6. The combination wet dry wipe of claim 5, wherein the separating layer is formed of thermoplastic material, wherein the adhesive comprises heat-melted thermoplastic material.

* * * * *